United States Patent
McEntire et al.

(10) Patent No.: US 9,353,010 B2
(45) Date of Patent: May 31, 2016

(54) ALUMINA-ZIRCONIA CERAMIC IMPLANTS AND RELATED MATERIALS, APPARATUS, AND METHODS

(71) Applicant: Amedica Corporation, Salt Lake City, UT (US)

(72) Inventors: Bryan J. McEntire, Sandy, UT (US); Ramaswamy Lakshminarayanan, West Jordan, UT (US); Ryan Bock, Salt Lake City, UT (US)

(73) Assignee: Amedica Corporation, Salt Lake City, UT (US)

( * ) Notice: Subject to any disclaimer, the term of this patent is extended or adjusted under 35 U.S.C. 154(b) by 131 days.

(21) Appl. No.: 14/213,769

(22) Filed: Mar. 14, 2014

(65) Prior Publication Data

US 2014/0265064 A1 Sep. 18, 2014

Related U.S. Application Data

(60) Provisional application No. 61/784,970, filed on Mar. 14, 2013.

(51) Int. Cl.
*C04B 35/119* (2006.01)
*C04B 35/10* (2006.01)
(Continued)

(52) U.S. Cl.
CPC ............. *C04B 35/10* (2013.01); *A61L 27/00* (2013.01); *A61L 27/10* (2013.01); *C04B 35/117* (2013.01); *C04B 35/119* (2013.01); *C04B 35/44* (2013.01); *C04B 35/62625* (2013.01); *C04B 35/62685* (2013.01); *C04B 35/6455* (2013.01); *A61L 2430/24* (2013.01); *C04B 2235/3206* (2013.01); *C04B 2235/3208* (2013.01); *C04B 2235/3213* (2013.01); *C04B 2235/3217* (2013.01); *C04B 2235/3222* (2013.01); *C04B 2235/3225* (2013.01); *C04B 2235/3229* (2013.01); *C04B 2235/3232* (2013.01);
(Continued)

(58) Field of Classification Search
CPC .............. C04B 35/119; C04B 2235/3206; C04B 2235/3208; C04B 2235/3213; C04B 2235/3225; C04B 2235/3246; C04B 2235/3229; C04B 2235/3232; C04B 2235/663; A61L 27/105
See application file for complete search history.

(56) References Cited

U.S. PATENT DOCUMENTS

| | | | |
|---|---|---|---|
| 4,298,385 | A | 11/1981 | Claussen et al. |
| 4,316,964 | A | 2/1982 | Lange |

(Continued)

OTHER PUBLICATIONS

ISO/DIS 6474-2.2—"Implants for surgery—Ceramic materials—Part 2: Composite materials based on a high purity alumina matrix with zirconia reinforcement," (2011).

(Continued)

*Primary Examiner* — Erin Snelting
(74) *Attorney, Agent, or Firm* — Phillips Ryther & Winchester; Matthew D. Thayne

(57) ABSTRACT

Embodiments of apparatus, systems, and methods relating to biomedical implants and other devices made up of unique and improved alumina-zirconia ceramic materials. In an example of a method according to an implementation of the invention, a slurry is prepared, compressed, and fired to obtain a fired ceramic piece comprising at least aluminum oxide, zirconium dioxide, yttrium oxide, cerium oxide, strontium oxide, magnesium oxide, titanium dioxide, and calcium oxide. Some embodiments and implementations may comprise selected concentrations of one or more such compounds to yield certain preferred results.

22 Claims, 1 Drawing Sheet

(51) Int. Cl.
  A61L 27/00    (2006.01)
  C04B 35/117   (2006.01)
  C04B 35/44    (2006.01)
  C04B 35/626   (2006.01)
  C04B 35/645   (2006.01)
  A61L 27/10    (2006.01)

(52) U.S. Cl.
  CPC .......... C04B 2235/3244 (2013.01); C04B 2235/6567 (2013.01); C04B 2235/663 (2013.01); C04B 2235/96 (2013.01)

(56) References Cited

U.S. PATENT DOCUMENTS

| | | | |
|---|---|---|---|
| 5,002,911 | A | 3/1991 | Matsumoto et al. |
| 5,830,816 | A | 11/1998 | Burger et al. |
| 6,387,132 | B1 | 5/2002 | Deppisch et al. |
| 6,452,957 | B1 | 9/2002 | Burger et al. |
| 7,012,036 | B2 | 3/2006 | Nawa et al. |
| 7,037,603 | B2 | 5/2006 | Lasater |
| 7,056,851 | B2 | 6/2006 | Nawa |
| 7,148,167 | B2 | 12/2006 | Shikata et al. |
| 7,297,420 | B2 | 11/2007 | Jiang |
| 7,435,443 | B2 | 10/2008 | Jiang |
| 7,820,577 | B2 | 10/2010 | Shikata et al. |
| 7,928,028 | B2 | 4/2011 | Nawa et al. |
| 8,093,168 | B2 | 1/2012 | Nawa et al. |
| 2002/0010070 | A1 | 1/2002 | Cales et al. |
| 2006/0046070 | A1 | 3/2006 | Jiang |
| 2006/0121206 | A1 | 6/2006 | Jiang |
| 2008/0118722 | A1* | 5/2008 | Shikata .......... C04B 35/119 428/212 |

OTHER PUBLICATIONS

M. Hirano, et. al.,"Hydrothermal Stability of Yttria- and Ceria-doped Tetragonal Zirconia-Alumina Composites," J. Mat. Sci., 26, 5047-5052, (1991).
M. Hirano, et. al., "Strength and Phase Stability of Yttria-Ceria-Doped Tetragonal Zirconia/Alumina Composites Sintered and Hot Isostatically Pressed in Argon—Oxygen Gas Atmosphere," J. Am. Ceram. Soc., 74, [3], 606-11, (1991).
M. Hirano, et. al., "Fracture Toughness, Strength and Vickers Hardness of Yttria-Ceria-Doped Tetragonal Zirconia/Alumina Composites Fabricated by Hot Isostatic Pressing," J. Mat. Sci., 27, 3511-3518, (1992).
R. A. Cutler, et. al., "High Toughness Ce-TZP/Al2O3 Ceramics with Improved Hardness and Strength," J. Am. Ceram. Soc., 74, [1], 179-86, (1991).
S. Deville, et. al., "Low Temperature Ageing of Zirconia-Toughened Alumina Ceramics and its Implication in Biomedical Implants," J. Eur. Ceram. Soc., 23, 2975-2982, (2003).
T. Sato, et. al., "Postsintering Hot Isostatic Pressing of Ceria-Doped Tetragonal Zirconia/Alumina Composites in an Argon—Oxygen Gas Atmosphere," J. Am. Ceram. Soc., 72, [5], 761-64, (1989).
M. Nawa, et. al., "Tough and Strong Ce-TZP/Aiumina Nanocomposties Doped with Titania," Ceramics International, 24,497-506, (1998).
M. N. Rahaman, et al., Ceramics for Prosthetic Hip and Knee Joint Replacement, J. Am. Ceram. Soc., 90, [7], 1965-1988, (2007).
B. Sonny Bal, et al. "Ceramic Materials in Total Joint Arthroplasty," Semin Arthro 17:94-101 (2006).
W. Rieger, "Ceramics in Orthopedics—30 Years of Evolution and Experience," in: C. Rieker, S. Oberholzer and U. Wyss, World Tribology Forum in Arthroplasty, Published by Hans Huber, Bern, Switzerland, 3-14, (2001).
I. C. Clarke, et al., "Structural Ceramics in Orthopedics," in Bone Implant Interface, Edited by H. U. Cameron, 203-252, (St. Louis: Mosby Press, 1994).
J. Charnley, "Arthroplasty of the Hip: A New Operation," Lancet, 1, [7187], 1129-32, (1961).
K. Tanaka, et. al., "Ce-TZP/Al2O3 Nanocomposite as a Bearing Material in Total Joint Replacement," J Biomed Mater Res (Appl Biomater) 63: 262-270, (2002).
N. Sugano, et. al., "Polyethylene Sockets and Alumina Ceramic Heads in Cemented Total Hip Arthroplasty, a Ten-Year Study," J. Bone & Joint Surg., 77-B, 548-56, (1995).
S. B. Murphy, et. al., "Two- to 9-Year Clinical Results of Alumina Ceramic-on-Ceramic THA," Clinical Orthopaedics and Related Research, [453], 97-102, (2006).
Standard Specification for High-Purity Dense Aluminum Oxide for Medical Applications, ASTM F 603-00, (West Conshohocken, PA: ASTM Press).
C. Piconi, et. al., Alumina and Zirconia Ceramics in Joint Replacements, J. App. Biomater. & Biomech., 1, 19-32, (2003).
R. S. Roy, et. al., "Sliding Wear Behavior of Submicron-Grained Alumina in Biological Environment," Published online Mar. 16, 2007; www.interscience.wiley.com; DOI: 10.1002/jbm.a.31230.
K-H. Koo, et. al., "Isolated Fracture of the Ceramic Head after Third Generation Alumina-on-Alumina Total Hip Arthroplasty," J. Bone Joint Surg. Am., (2008), 90:329-336; doi:10.2106/JBJS.F.01489.
J. Garino, et. al., The Reliability of Modern Alumina Bearings in Total Hip Arthroplasty, Semin. Arthro. 17,113-119, (2006).
R. C. Garvie, et. al., "Biocompatibility of Magnesia—Partially Stabilized Zirconia (Mg-PSZ) Ceramics," J. Mater. Sci., 19, [10], 3224-28, (1984).
T. Masaki, "Mechanical Properties of Toughened $ZrO_2$—$Y_2O_3$ Ceramics," J. Am. Ceram. Soc., 69, [8], 638-40, (1986).
B. Cales, "Zirconia Ceramic for Improved Hip Prosthesis—A Review," in: 6lh Biomaterial Symposium, Ceramic Implant Materials in Orthopaedic Surgery, 2-71, (Gottingen, Germany, 1994).
C. B. Rieker, et. al., "Wear Behaviour of New Generation Ceramics," in: Ceramics in Orthopaedics, 81h Biolox Symposium Proceedings, H. Zippel and M. Dietrich, Eds., 19-24, (Darmstadt: Steinkopff Verlag, 2003).
M. J. Kraay, et. al., "Zirconia versus Co—Cr Femoral Heads in Total Hip Arthroplasty," Clinical Orth. & Related Res., 453, 86-90, (2006).
R. H. J. Hannink, et. al., "Transformation Toughening in Zirconia-Containing Ceramics," J. Am. Ceram. Soc., 83, [3], 461-87, (2000).
Standard Specification for High-Purity Dense Magnesia Partially Stabilized Zirconia (Mg-PSZ) for Surgical Implant Applications, ASTM F2393-10, (West Conshohocken, PA: ASTM Press).
Standard Specification for High-Purity Dense Yttria Tetragonal Zirconium Oxide Polycrystal (Y-TZP) for Surgical Implant Applications, ASTM F1873-98, Withdrawn 2007, (West Conshohocken, PA: ASTM Press).
J. Chevalier, et. al., "The Tetragonal-Monoclinic Transformation in Zirconia: Lessons Learned and Future Trends," J. Am. Ceram. Soc., 92, [9], 1901-1920, (2009).
E. M. Santos, et. al., "Examination of Surface and Material Properties of Explanted Zirconia Femoral Heads," J. Arthroplasty, 19, [7], Suppl. 2, 30-34, (2004).
G. Maccauro, et. al., "Fracture of a Y-TZP Ceramic Femoral Head," J. Bone Joint Surg., 86, 1192-6, (2004), doi:10.1302/0301-620X. 86B8.
S. Hori, et. al., "Strength-Toughness Relations in Sintered and Isostatically Hot-Pressed $ZrO_2$-Toughened $Al_2O_3$," J. Am. Ceram. Soc., 69, [3], 169-72, (1986).
G. Magnani, et.al., "Effect of the Composition and Sintering Process on Mechanical Properties and Residual Stresses in Zirconia-Alumina Composites," J. Eur. Ceram. Soc., 25, 3383-3392, (2005).
See Metoxit Zirconia Data Sheet, http://www.metoxit.com/english/downloads/mat zr e.pdf.
M. Kuntz, et. al., "Controlled Zirconia Phase Transformation in BIOLOX delta-a Feature of Safety," in Bioceramics and Alternative Bearings in Joint Arthroplasty, 10th Biolox Symposium Proceedings, 79-83, (Darmstadt, Steinkopff Verlag Press, 2005).
G. Willmann, et. al., "Biocompatibility of a New Alumina Matrix Biocomposite AMC," Proceedings of the 13lh Int. Symp. on Ceramics in Medicine, Bologna, Italy, Nov. 22-26, 2000, pp. 569-572, (Switzerland: Trans Tech Publications, 2001).
H. Kamiya, et. al., "Erosion Wear Properties of Tetragonal $ZrO_2$-($Y_2O_3$)-Toughened $Al_2O_3$ Composites," J. Am. Ceram. Soc., 77, [3], 666-72, (1994).

(56) References Cited

OTHER PUBLICATIONS

B. Kerkwijk, et. al., "Processing of Homogeneous Zirconia-Toughened Alumina Ceramics with High Dry-Sliding Wear Resistance," J. Am. Ceram. Soc., 82, [8], 2087-93, (1999).

G. M. Insley, et. al., "In-Vitro Testing and Validation of Zirconia Toughened Alumina (ZTA)," in: Bioceramics in Joint Arthroplasty, 26-31, Proceedings of the ih Int. Biolox Symposium, Mar. 15-16, 2002, J.P. Garino and G. Willmann, Eds., (Stuttgart: Georg Thieme Verlag, 2002).

I.C. Clarke, et. al., "Severe Simulation Test for Run-In Wear of All Alumina Compared to Alumina Composite THR," in: 10th Biolox Symposium Proceedings, 11-20, (Darmstadt, Steinkopff Verlag Press, 2005).

I. C. Clarke, et. al., "US Perspective on Hip Simulator Wear Testing of Biolox Delta in 'Severe' Test Modes," in: Ceramics in Orthopaedics, 11th Biolox Symposium Proceedings, Jun. 30- Jul. 1, 2006, F. Benazzo, F. Falez and M. Dietrich, Eds., (Darmstadt, Steinkopff Verlag, 2006).

I. C. Clarke, et. al., "Hip Simulator Wear Studies of an Alumina-Matrix Composite (AMC) Ceramic Compared to Retrieval Studies of AMC Balls with 1-7 Years Follow-Up," Wear, 267, 702-709, (2009).

G. Pezzotti, et. al., "Raman Spectroscopic Analysis of Advanced Ceramic Composite for Hip Prosthesis," J. Am. Ceram. Soc., 91, [4], 1199-1206, (2008).

G. Pezzotti, et. al., "Fracture Toughness Analysis of Advanced Ceramic Composite for Hip Prosthesis," J. Am. Ceram. Soc., 92, [8], 1817-1822, (2009).

J. Chevalier, et. al, "On the Kinetics and Impact of Tetragonal to Monoclinic Transformation in an Alumina/Zirconia Composite for Arthroplasty Applications," Biomaterials, 30, 5279-82, (2009).

G. Pezzotti, et. al., "Nano-Scale Topography of Bearing Surface in Advanced Alumina/Zirconia Hip Joint Before and After Severe Exposure in Water Vapor Environment," J. Orthop. Res., 28, 762-766 (2010).

G. Pezzotti, et. al., "Surface Topology of Advanced Alumina/Zirconia Composite Femoral Head as Compared with Commercial Femoral Heads Made of Monolithic Zirconia," J. Am. Ceram. Soc., 94, [3], 945-950, (2011).

M. Kuntz, "Validation of a New High Performance Alumina Matrix Composite for use in Total Joint Replacement," Semin. Arthro. 17, 141-145, (2006).

I. Papageorgiou, et. al., "The Effect of Nano- and Micron-Sized Particles of Cobalt—Chromium Alloy on Human Fibroblasts In Vitro," Biomaterials, 28, 2946-2958, (2007).

S. K. Hwang, et. al., "Fracture-Dissociation of Ceramic Liner," Orthopedics, 31, [8], 804.

W.G. Hamilton, et. al., "THA With Delta Ceramic on Ceramic: Results of a Multicenter Investigational Device Exemption Trial," C/in. Orthop. Relat. Res.; 468, [2], 358-366, (2010).

A. V. Lombardi, et. al., "Delta Ceramic-on-Alumina Ceramic Articulation in Primary THA," C/in. Orthop. Relat. Res.; 468, [2], 367-374, (2010).

V. Lughi, et. al., "Low Temperature Degradation—Aging—of Zirconia: A Critical Review of the Relevant Aspects in Dentistry," Dental Materials, 26, 807-820, (201 0).

C. Pecharroman, et. al., "Percolative Mechanism of Aging in Zirconia Containing Ceramics for Medical Applications," Adv. Mater., 15, [6], 507-11, (2003).

N. Claussen, "Fracture Toughness of Al203 with Unstabilized Zr02 Dispersed Phase," J. Am. Ceram. Soc., 59, [1-2], 49-51, (1976).

* cited by examiner

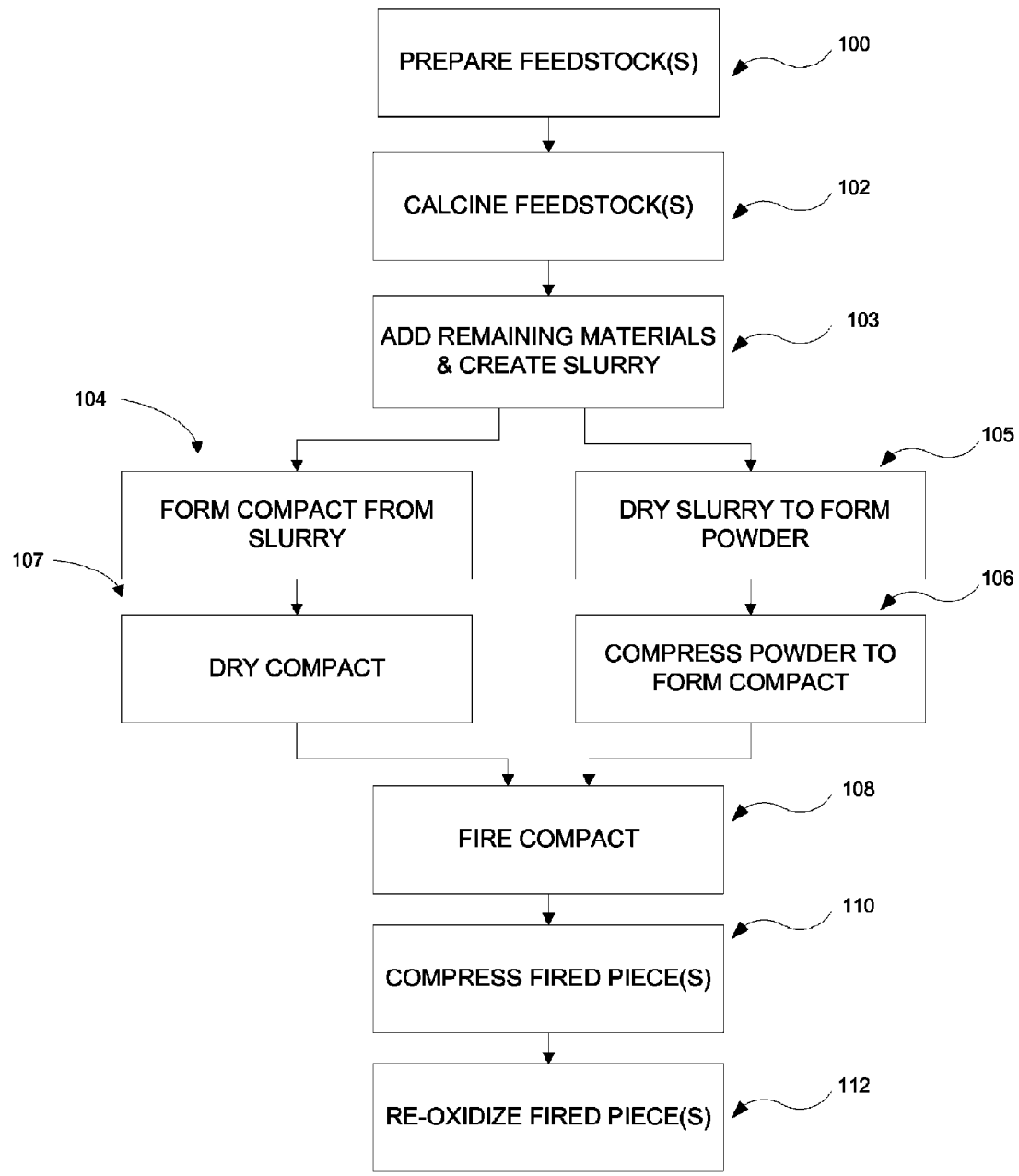

ALUMINA-ZIRCONIA CERAMIC IMPLANTS AND RELATED MATERIALS, APPARATUS, AND METHODS

RELATED APPLICATIONS

This application claims the benefit under 35 U.S.C. §119 (e) of U.S. Provisional Patent Application No. 61/784,970 filed Mar. 14, 2013, and titled "ALUMINA-ZIRCONIA CERAMIC IMPLANTS AND RELATED MATERIALS, APPARATUS, AND METHODS," which application is incorporated herein by reference in its entirety.

SUMMARY

Disclosed herein are embodiments of apparatus, methods, and systems relating to biomedical implants and other devices made up of unique and improved alumina-zirconia ceramic materials. In some embodiments, biomedical implants, or one or more portions of a biomedical implant, may be manufactured using such alumina-zirconia ceramic materials. Such implants may have improved fracture strengths and/or toughnesses, and may also, or alternatively, have improved resistance to low-temperature degradation (LTD).

In one example of a method for manufacturing a ceramic biomedical implant, the method may comprise preparing a first feedstock by mixing ingredients comprising at least aluminum oxide and strontium carbonate or ingredients selected to yield aluminum oxide and strontium carbonate. A second feedstock may also be prepared by mixing ingredients comprising at least aluminum oxide and calcium carbonate or ingredients selected to yield aluminum oxide and calcium carbonate. In some implementations, the feedstock(s) may be prepared using, for example, vibratory, ball, or attrition milling in water with appropriate dispersants for about 8 to about 24 hours.

In some implementations, the feedstock(s) may be calcined. This step may be performed, for example, in air at between about 1100° C. and about 1300° C. for approximately 2 hours.

A slurry may be prepared comprising materials from the first feedstock, materials from the second feedstock, and further comprising additional ingredients configured to yield at least a portion of a ceramic biomedical implant comprising at least aluminum oxide, zirconium dioxide, yttrium oxide, cerium oxide, strontium oxide, magnesium oxide, titanium dioxide, and calcium oxide. In some embodiments, certain biomedical implants may comprise this combination of materials. In some such embodiments, such biomedical implants may be manufactured using the precise concentrations and/or concentration ranges disclosed below. Thus, various embodiments of the invention are contemplated in which ceramic pieces and/or biomedical implants comprise one or more such concentrations and/or concentration ranges.

The step of creating the slurry may further comprise subjecting the feedstock(s), in combination with the remaining raw materials (together, the slurry), to vibratory, ball, or attrition milling for about 8 to about 24 hours in water, along with appropriate dispersants.

A compact may then be formed derived from the slurry. The slurry may, for example, be formed into a compact by compressing and/or drying the slurry. The slurry may be compressed, for example, by way of a uniaxial or isostatic compaction method. This compression may be at pressures between about 130 MPa and about 400 MPa. In some such embodiments and implementations, the compression may be at pressures between about 200 MPa and about 400 MPa.

In some embodiments and implementations, the step of forming the compact derived from the slurry may comprise forming the compact directly from the slurry, as mentioned above. In other embodiments and implementations, the step of forming the compact derived from the slurry may comprise drying the slurry to form a powder and then compressing the powder to form the compact.

The compact/composition/slurry may then be fired. In some embodiments, this firing may be between about 1450° C. and about 1600° C. and the firing may take place for up to about 2 hours.

After firing, the fired piece(s) may further densified via, for example, hot isostatic compressing, which may be done at temperatures of between about 1400° C. and about 1500° C. in nitrogen and/or argon at pressures of between about 130 MPa to about 210 MPa for about 1 to 2 hours.

The fired piece(s) may then be reoxidized. This step may take place in, for example, an electric air atmosphere kiln at temperatures of between about 1250° C. and about 1400° C. for time periods ranging between about 2 to about 64 hours. In some embodiments, following the step of reoxidizing the fired piece, the fired piece may comprise at least aluminum oxide, zirconium dioxide, yttrium oxide, cerium oxide, strontium oxide, magnesium oxide, titanium dioxide, and calcium oxide. In some such embodiments, the concentrations of these compounds in the fired piece may be as outlined below.

In another example of a method for manufacturing a ceramic piece, the method may comprise preparing a slurry comprising ingredients configured to yield a ceramic piece comprising at least aluminum oxide, zirconium dioxide, yttrium oxide, cerium oxide, strontium oxide, magnesium oxide, titanium dioxide, and calcium oxide. A compact may then be formed derived from the slurry (by, for example, compressing the slurry to for the compact and then drying the compact or first drying the slurry to form a powder and then compressing the powder to form the compact) and then fired to obtain a fired ceramic piece. The fired ceramic piece may comprise at least aluminum oxide, zirconium dioxide, yttrium oxide, cerium oxide, strontium oxide, magnesium oxide, titanium dioxide, and calcium oxide.

In some embodiments and implementations, the fired ceramic piece may comprise aluminum oxide in a concentration of at least about 74% by weight. In some such embodiments and implementations, the fired ceramic piece may comprise aluminum oxide in a concentration of at least about 74.6% by weight.

In some embodiments and implementations, the fired ceramic piece may comprise a combination of aluminum oxide, strontium oxide, magnesium oxide, titanium dioxide, and calcium oxide in a concentration of at least about 84% by volume.

In some embodiments and implementations, the fired ceramic piece may comprise yttrium oxide in a concentration of between about 0.8% and about 1.5% by mole of the total molar amounts of zirconium dioxide, yttrium oxide, and cerium oxide in the fired ceramic piece.

In some embodiments and implementations, the fired ceramic piece may comprise cerium oxide in a concentration of between about 1.75% and about 4.0% by mole of the total molar amounts of zirconium dioxide, yttrium oxide, and cerium oxide in the fired ceramic piece.

In some embodiments and implementations, the fired ceramic piece may comprise strontium oxide in a concentration of between about 0.8% and about 1.2% by weight.

In some embodiments and implementations, the fired ceramic piece may comprise strontium oxide in a concentration of about 0.8% by weight.

In some embodiments and implementations, the fired ceramic piece may comprise magnesium oxide in a concentration of about 0.05% by weight.

In some embodiments and implementations, the fired ceramic piece may comprise titanium dioxide in a concentration of about 0.10% by weight.

In some embodiments and implementations, the fired ceramic piece may comprise calcium oxide in a concentration of about 0.15% by weight.

In some embodiments and implementations, the fired ceramic piece may comprise magnesium oxide, titanium dioxide, and calcium oxide in a combined concentration of no more than about 0.3% by weight.

In some embodiments and implementations, the fired ceramic piece may comprise strontium oxide in a concentration of between about 0.8% and about 1.2% by weight. In some such embodiments and implementations, the fired ceramic piece may comprise strontium oxide in a concentration of about 0.8% by weight.

In some embodiments of biomedical implants and/or other ceramic pieces manufactured according to one or more of the principles disclosed herein, such embodiments may comprise a 3-point flexural strengths of at least about 1,000 MPa and a fracture toughness of at least about 6.5 MPa·m$^{1/2}$. In some such embodiments, the fracture toughness may exceed about 8 MPa·m$^{1/2}$. In some such embodiments, the fracture toughness may exceed about 10 MPa·m$^{1/2}$. In some such embodiments, the fracture toughness may exceed about 11 MPa·m$^{1/2}$. In some such embodiments, the fracture toughness may exceed about 11.4 MPa·m$^{1/2}$. Several such embodiments also exhibit minimal low temperature hydrothermal degradation after being exposed to saturated steam autoclave environments of 120° to 134° C. for up to 100 hours. In some embodiments, the 3-point flexural strength may be at least about 1,100 MPa. In some embodiments, the 3-point flexural strength may be at least about 850 MPa.

BRIEF DESCRIPTION OF THE DRAWINGS

The written disclosure herein describes illustrative embodiments that are non-limiting and non-exhaustive. Reference is made to certain of such illustrative embodiments that are depicted in the FIGURES, in which:

FIG. 1 is a flow chart illustrating one example of a method for manufacturing an alumina-zirconia ceramic material suitable for use as a biomedical implant.

DETAILED DESCRIPTION

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Various embodiments of apparatus, materials, methods, and systems are disclosed herein that relate to biomedical implants and other devices made up of unique alumina-zirconia ceramic materials. In some embodiments, these materials may be used to form various structural members, such as human endoprostheses and other biomedical implants. Examples of such implantable devices that may benefit from one or more of the unique materials and/or methods disclosed herein include, but are not limited to, artificial hips, knees, shoulders, ankles and phalange joints, spinal articulation devices and other spinal implants, and dental implants, such as abutments, crowns, and bridges. The compositions and processing methods provided in this disclosure may provide devices that have high fracture strength and toughness, and have improved resistance to low-temperature degradation (LTD).

Alumina ($Al_2O_3$) has become one of the most widely used ceramic materials for total hip arthroplasty. An industrial specification was developed for its composition, processing and properties, and it has been shown to be biocompatible and to possess high hardness and a low coefficient of friction. These characteristics reduce the occurrence of wear debris. However, alumina also has a relatively low fracture strength and toughness, both of which increase the risk of catastrophic in-vivo failure.

To overcome this problem, zirconia ($ZrO_2$) was investigated and added as an alternative ceramic, either in its partially stabilized form using magnesia, or with yttria to form Tetragonal Zirconia Polycrystals (TZP). These compositions greatly improved upon the strength and toughness of alumina and, moreover, they had lower coefficients of friction and wear. These materials derived much of their improved characteristics by taking advantage of a polymorphic phase transformation that occurs in doped-zirconia known as transformation-toughening. This transformation involves the metastabilization of the high-temperature tetragonal phase through the incorporation of magnesia, yttria, or other dopants.

In the presence of an advancing crack, the metastable tetragonal phase transforms to its stable monoclinic form, typically with an accompanying volume increase of about 5%. This sudden volume change exerts compressive forces on the crack tip, thereby slowing or arresting its propagation. Partially stabilized zirconia ("PSZ") implants are still available, and an industrial standard for their composition, processing, and properties has been created. However, after more than a decade of use, TZP implants were withdrawn from the marketplace in 2001, and the industrial standard supporting their use has since been abandoned. The abandonment of TZP is attributable primarily to one severe weakness—it spontaneously transforms to its stable monoclinic form under in-vivo hydrothermal conditions. This effect has become known as low-temperature degradation (LTD). This transformation results in increased implant surface roughness, enhanced wear, weakening of the material, and often eventual fracture.

Zirconia-Toughened Alumina (ZTA) and Alumina Matrix Composites (AMC) were then introduced to the marketplace in an attempt to overcome TZP's limitations. ZTA is a fully dense composite ceramic consisting typically of TZP in an alumina matrix. AMC is a special ZTA composition consisting of $ZrO_2$ and mixed oxides consisting of $Y_2O_3$, $Cr_2O_3$, and SrO, along with $Al_2O_3$.

ZTA/AMC materials are bio-inert, and typically have good strength, toughness, and hardness properties. These materials are also often highly abrasion- and wear-resistant. For total hip arthroplasty ("THA devices"), ZTA/AMC components typically provide equivalent or lower wear rates than alumina or TZP. However, ZTA and AMC also achieve their mechanical property improvements through transformation toughening, and concerns remain about their in-vivo hydrothermal stability.

As such, various embodiments disclosed herein may provide for an alumina zirconia composite composition and/or related processing methods that may be used to form ceramic implants with high fracture strength, high toughness, and improved resistance to low-temperature hydrothermal degradation.

In some embodiments, the $Al_2O_3$ concentration in the composition is greater than about 75% of the entire composition by weight. In some embodiments the $Al_2O_3$ concentration in the composition is greater than about 74% of the entire composition by weight. In some such embodiments, the $Al_2O_3$ concentration in the composition is greater than about 74.6% of the entire composition by weight. It is anticipated, however, that the desired percentage of alumina may vary in accordance with the variance of other ingredients that may also be included in the composition, such as SrO, MgO, $TiO_2$, CaO, $ZrO_2$, $Y_2O_3$, and $CeO_2$.

In some embodiments, the combination of $Al_2O_3$, SrO, MgO, $TiO_2$, and CaO is greater than about 84% of the entire composition by volume. Keeping these constituents above this volumetric concentration appears to substantially eliminate, or at least minimize, water percolation into the ceramic body, and thereby minimizes LTD.

In some embodiments, the $ZrO_2$ content may be within a range of between about 21% of the entire composition by weight and about 24% of the entire composition by weight. In some embodiments, stabilization additives may be added to the composition. For example, $Y_2O_3$, and/or $CeO_2$ may be added as stabilization additives. In some such embodiments, the combination of $ZrO_2$ and stabilization additives may be less than or equal to about 16% of the entire composition by volume. Thus, for example, in some such embodiments, the combination of the $ZrO_2$ along with $Y_2O_3$, and/or $CeO_2$ may be less than or equal to about 16% of the entire composition by volume. These particular compositions appear to substantially eliminate, or at least minimize, LTD through percolation.

In some embodiments, the $Y_2O_3$ content may be within a range of between about 0.8% and about 1.5% by mole based on the total molar amounts in the composition. For example, in embodiments containing $ZrO_2$, $CeO_2$ and $Y_2O_3$, the $Y_2O_3$ content may be within a range of between about 0.8% and about 1.5% of the total molar amounts of $ZrO_2$, $CeO_2$ and $Y_2O_3$ combined. For certain applications, it appears that lower concentrations of $Y_2O_3$ may not provide sufficient stabilization, whereas higher concentrations may lead to an enhancement of the detrimental effects of LTD.

In some embodiments, the concentration of ceria ($CeO_2$) may be within a range of between about 1.75% and about 4.0% by mole based on the total molar amounts in the composition. For example, in embodiments containing $ZrO_2$, $CeO_2$ and $Y_2O_3$, the $CeO_2$ content may be within a range of between about 1.75% and about 4.0% by mole based on the total molar amounts of $ZrO_2$, $CeO_2$ and $Y_2O_3$. For certain applications, it appears that lower concentrations of $CeO_2$ may not provide sufficient protection against LTD, whereas higher concentrations can result in cracking of the ceramic body during re-oxidation heat treatments subsequent to hot isostatic pressing in a reducing environment.

In some embodiments, the concentration of strontia (SrO) may be between about 0.8% and about 1.2% of the entire composition by weight. In some such embodiments, the concentration of SrO may be equal to about 0.8% of the entire composition by weight. In some implementations of desired methods in accordance with the present disclosure, SrO may be added to the composition as strontium aluminate ($SrAl_2O_4$). The addition of this ingredient may be desirable for certain applications to provide platelet type grains, which may provide additional strength and toughness to the ceramic body.

In some embodiments, the concentration of magnesia (MgO) may be less than or equal to about 0.05% of the entire composition by weight. In some such embodiments, the concentration of MgO may be equal to about 0.05% of the entire composition by weight. MgO may be added to the composition as a sintering aid and may also serve as an alumina grain growth inhibitor. In some implementations of desired methods in accordance with the present disclosure, MgO may be added to the composition as magnesium aluminate ($MgAl_2O_4$).

In some embodiments, the concentration of titania ($TiO_2$) may be less than or equal to about 0.10% of the entire composition by weight. In some such embodiments, the concentration of $TiO_2$ may be equal to about 0.10% of the entire composition by weight. $TiO_2$ may also be added to the composition as a sintering aid.

In some embodiments, the concentration of Calcia (CaO) may be about 0.15% of the entire composition by weight. CaO may also be added to the composition as a sintering aid. In some implementations of desired methods in accordance with the present disclosure, CaO may be added to the composition as calcium aluminate ($CaAl_2O_4$).

In embodiments containing MgO in combination with $TiO_2$ and CaO, these ingredients may form a low melting eutectic that may serve to lower the sintering temperature and may further allow for the production of a ceramic body with a finer grain size, higher fracture strength, and toughness. For certain applications, it may be desirable to keep the total concentration of the combination of the sintering aids at less than or equal to about 0.3% of the entire composition by weight. For example, in some embodiments, the total combined concentration of MgO, $TiO_2$, and CaO may be less than or equal to about 0.3% of the entire composition by weight.

In some embodiments, the combination of sintering aids may be equal to about 0.3% of the entire composition by weight. In some such embodiments, the combination of MgO, $TiO_2$, and CaO may be approximately equal to about 0.3% of the entire composition by weight. In other embodiments, the combination of sintering aids may be less than 0.3% of the entire composition by weight. For example, the combination of MgO, $TiO_2$, and CaO may be less than 0.3% of the entire composition by weight.

For some implementations, concentrations of these ingredients (or the combination of other sintering aids) higher than about 0.3% of the entire composition by weight may lead to the development of a glassy grain-boundary phase in the dense ceramic, which may potentially result in lower strength and toughness, whereas concentrations significantly lower than about 0.3% of the entire composition by weight may be insufficient to provide for adequate densification.

In one specific example of a composition according to one or more of the principles disclosed herein, the composition may comprise about 21.19% by weight of $ZrO_2$, about 0.37% by weight of $Y_2O_3$, about 1.20% by weight of $CeO_2$, about 1.59% by weight of $SrAl_2O_4$, about 0.14% by weight of $CaAl_2O_4$, about 0.18% by weight of $MgAl_2O_4$, about 0.10% by weight of $TiO_2$, and about 75.23% by weight of $Al_2O_3$. This composition may comprise about 95.22 mol % of $ZrO_2$, about 0.91 mol % of $Y_2O_3$, and about 3.87 mol % of $CeO_2$ within the phase comprising zirconium dioxide, yttrium oxide, and cerium oxide. It should be understood, however, that these percentages and/or ingredients may vary in other implementations and embodiments, as suggested elsewhere in this disclosure.

A particular exemplary method for creating a ceramic implant is illustrated in FIG. 1. In this method, one or more feedstocks may be prepared for the $SrAl_2O_4$ and $CaAl_2O_4$ at 100 by mixing $SrCO_3$ and/or $CaCO_3$ with $Al_2O_3$, respectively. In some implementations, one may start with raw $CaAl_2O_4$ and $SrAl_2O_4$. Alternatively, it is possible to use SrO and $Al_2O_3$, along with CaO and $Al_2O_3$.

In some implementations of methods for creating a ceramic material, such as a ceramic implant, having these or other ingredients, commercially available ceramic powders may be used, such as Tosoh™ TZ-0 or TZ-3Y (Tokyo, Japan) or Inframat™ Advanced Materials (Manchester, Conn.) 0 and 3 mol % $ZrO_2$, may be used. Additionally, or alternatively, Inframat™ $CeO_2$, Spectrum Chemical™ (Los Angeles, Calif.), $CaCO_3$, $SrCO_3$ and $TiO_2$, Sasol Ceralox™ (Tuscon, Ariz.) AHPA-0.5 $Al_2O_3$, and/or AHPA Spinel™ AF ($MgAl_2O_4$) may be used.

The feedstock(s) may be prepared using, for example, vibratory, ball, or attrition milling in water with appropriate dispersants for about 8 to about 24 hours. Many such dispersants may be used, as those of ordinary skill in the art will appreciate. For example, a combination of ammonium hydroxide and citric acid may be used for certain implementations, which may be desirable for performing a suitable pH adjustment. The step 100 of preparing the feedstock(s) may further comprise centrifuging the mixed constituents to remove excess water, after which the resulting cakes may be dried in an oven. A dry-ball mill deagglomeration step may then be conducted to break down soft agglomerates.

The feedstock(s) may then be calcined, as indicated at step 102. In some implementations, step 102 may comprise calcining the feedstock(s) in air at between about 1100° C. and about 1300° C. for approximately 2 hours.

The feedstock(s) may then be weighed and added to the batch in their appropriate proportions, along with the remaining constituents, as indicated at step 103, to create a slurry.

The step of creating the slurry may further comprise subjecting the feedstock(s), in combination with the remaining raw materials (together, the slurry), to vibratory, ball, or attrition milling for about 8 to about 24 hours in water, along with appropriate dispersants. A binder may also be added to the batch at the end of the mixing/milling operations, after which the slurry containing the constituents may be dried. Various binders may be used, as those of ordinary skill in the art will appreciate. For example, in some implementations, an acrylic copolymer known under the name Rhoplex B-60A™ may be used.

In some implementations, the slurry may be dried to form a dried slurry or powder, as indicated at step 105. This step may comprise spray drying the slurry. The drying may take place, for example, in a conventional countercurrent, two fluid nozzle atomization spray dryer. The material may then be sieved. An external lubricant may also be added, if desired, such as Acrawax C™.

As indicated at step 106, the dried slurry or powder may then be compressed at pressures of, for example, between about 130 MPa and about 400 MPa using any suitable methodology, such as a uniaxial or isostatic compaction method. The resultant compact may then be fired in a kiln, as indicated at step 108. Step 108 may comprise, for example, use of an electric air atmosphere kiln. The temperature in such a kiln may be between about 1450° C. and about 1600° C. and the firing may take place for up to about 2 hours.

As an alternative to steps 105 and 106, a compact may be formed from the slurry at step 104, after which the compact may be dried at step 107.

After the firing step 108, the fired compact(s)/piece(s) may be compressed, as indicated at step 110. In preferred implementations, the fired piece(s) may be hot isostatically pressed at temperatures of between about 1400° C. and about 1500° C. in nitrogen at pressures of between about 130 MPa to about 210 MPa for about 1 to 2 hours.

The piece(s) may then be re-oxidized at step 112. The re-oxidation step 112 may take place in, for example, an electric air atmosphere kiln. The re-oxidation step 112 may also take place at temperatures of between about 1250° C. and about 1400° C. for time periods ranging between about 2 to about 64 hours.

It has been discovered that many components, such as biomedical implants, produced and processed according to one or more principles, implementations, or embodiments of this disclosure have 3-point flexural strengths of at least about 1,000 MPa and fracture toughnesses of at least about 6.5 $MPa \cdot m^{1/2}$. In some such embodiments, the fracture toughness may exceed about 8 $MPa \cdot m^{1/2}$. In some such embodiments, the fracture toughness may exceed about 10 $MPa \cdot m^{1/2}$. In some such embodiments, the fracture toughness may exceed about 11 $MPa \cdot m^{1/2}$. In some such embodiments, the fracture toughness may exceed about 11.4 $MPa \cdot m^{1/2}$. Several such embodiments also exhibit minimal low temperature hydrothermal degradation after being exposed to saturated steam autoclave environments of 120° to 134° C. for up to 100 hours. In some embodiments, the 3-point flexural strength may be at least about 1,100 MPa. In some embodiments, the 3-point flexural strength may be at least about 850 MPa.

EXAMPLE 1

In a first working example, several embodiments of ceramic components manufactured using the principles disclosed herein were created and tested for strength and toughness. The average three-point bend strength of these devices was about 1,013 MPa. After autoclaving at about 132-133° C. in 0.2 MPa of water vapor for 34 hours, the three-point average bend strength was about 1,018 MPa. The conditions for this autoclave test exceeded those specified in ISO 6474-2.2, which includes exposure to water vapor at 134±2° C. for a period of only 10 hours. The average fracture toughness of these devices was about 11.4 $MPa \cdot m^{1/2}$.

EXAMPLE 2

In a second working example, several embodiments of ceramic components were again manufactured using the principles disclosed herein and were created and tested for strength and toughness. The average three-point bend strength of these devices was about 918 MPa. The average fracture toughness of these devices was about 10.0 $MPa \cdot m^{1/2}$. Autoclave testing was not completed for this batch.

Ceramic components formed in accordance with one or more principles, implementations, or embodiments of this disclosure can be shaped and machined into useful human endoprostheses, including but not limited to artificial hips, knees, shoulders, ankles and phalange joints, and/or articulation devices in the spine, as well as dental implants, abutments, crowns and bridges.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment. Unless otherwise noted, the terms "a" or "an" are to be construed as meaning "at least one of." In addition, for ease of use, the words "including" and "having" are interchangeable with and have the same meaning as the word "comprising." Recitation of the term "first" with respect to a feature or element does not necessarily imply the existence of a second or additional such feature or element.

Similarly, it should be appreciated that in the above description of embodiments, various features are sometimes grouped together in a single embodiment, FIGURE, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment.

It will be apparent to those having skill in the art that changes may be made to the details of the above-described embodiments without departing from the underlying principles set forth herein. The scope of the present invention should, therefore, be determined only by the following claims.

The invention claimed is:

1. A method for manufacturing a ceramic biomedical implant, the method comprising the steps of:
   preparing a first feedstock by mixing ingredients comprising at least aluminum oxide and strontium carbonate or ingredients selected to yield aluminum oxide and strontium carbonate;
   preparing a second feedstock by mixing ingredients comprising at least aluminum oxide and calcium carbonate or ingredients selected to yield aluminum oxide and calcium carbonate;
   preparing a slurry comprising materials from the first feedstock, materials from the second feedstock, and further comprising additional ingredients configured to yield at least a portion of a ceramic biomedical implant comprising at least aluminum oxide, zirconium dioxide, yttrium oxide, cerium oxide, strontium oxide, magnesium oxide, titanium dioxide, and calcium oxide;
   forming a compact derived from the slurry;
   firing the compact to obtain a fired piece;
   after the step of firing the slurry, compressing the fired piece; and
   reoxidizing the fired piece, wherein, following the step of reoxidizing the fired piece, the fired piece comprises at least aluminum oxide, zirconium dioxide, yttrium oxide, cerium oxide, strontium oxide, magnesium oxide, titanium dioxide, and calcium oxide, and wherein the fired piece comprises a combination of aluminum oxide, strontium oxide, magnesium oxide, titanium dioxide, and calcium oxide in a concentration of at least about 84% by volume.

2. The method of claim 1, wherein the fired piece comprises aluminum oxide in a concentration of at least about 74% by weight.

3. The method of claim 1, wherein the fired piece comprises aluminum oxide in a concentration of at least about 74.6% by weight.

4. The method of claim 1, wherein the fired piece comprises yttrium oxide in a concentration of between about 0.8% and about 1.5% by mole of the total molar amounts of zirconium dioxide, yttrium oxide, and cerium oxide in the fired piece.

5. The method of claim 1, wherein the fired piece comprises cerium oxide in a concentration of between about 1.75% and about 4.0% by mole of the total molar amounts of zirconium dioxide, yttrium oxide, and cerium oxide in the fired piece.

6. The method of claim 1, wherein the fired piece comprises strontium oxide in a concentration of between about 0.8% and about 1.2% by weight.

7. The method of claim 6, wherein the fired piece comprises strontium oxide in a concentration of about 0.8% by weight.

8. The method of claim 1, wherein the step of forming the compact derived from the slurry comprises forming the compact from the slurry.

9. The method of claim 1, wherein the step of forming the compact derived from the slurry comprises:
   drying the slurry to form a powder; and
   compressing the powder to form the compact.

10. A method for manufacturing a ceramic piece, the method comprising the steps of:
    preparing a slurry comprising ingredients configured to yield a ceramic piece comprising at least aluminum oxide, zirconium dioxide, yttrium oxide, cerium oxide, strontium oxide, magnesium oxide, titanium dioxide, and calcium oxide;
    forming a compact derived from the slurry; and
    firing the compact to obtain a fired ceramic piece comprising at least aluminum oxide, zirconium dioxide, yttrium oxide, cerium oxide, strontium oxide, magnesium oxide, titanium dioxide, and calcium oxide, wherein the fired ceramic piece comprises strontium oxide in a concentration of between about 0.8% and about 1.2% by weight.

11. The method of claim 10, wherein the fired ceramic piece comprises aluminum oxide in a concentration of at least about 74.6% by weight.

12. The method of claim 10, wherein the fired ceramic piece comprises a combination of aluminum oxide, strontium oxide, magnesium oxide, titanium dioxide, and calcium oxide in a concentration of at least about 84% by volume.

13. The method of claim 10, wherein the fired ceramic piece comprises yttrium oxide in a concentration of between about 0.8% and about 1.5% by mole of the total molar amounts of zirconium dioxide, yttrium oxide, and cerium oxide in the fired ceramic piece.

14. The method of claim 10, wherein the fired ceramic piece comprises cerium oxide in a concentration of between about 1.75% and about 4.0% by mole of the total molar amounts of zirconium dioxide, yttrium oxide, and cerium oxide in the fired ceramic piece.

15. The method of claim 10, wherein the fired ceramic piece comprises strontium oxide in a concentration of about 0.8% by weight.

16. The method of claim 10, wherein the fired ceramic piece comprises magnesium oxide in a concentration of about 0.05% by weight.

17. The method of claim 10, wherein the fired ceramic piece comprises titanium dioxide in a concentration of about 0.10% by weight.

18. The method of claim 10, wherein the fired ceramic piece comprises calcium oxide in a concentration of about 0.15% by weight.

19. The method of claim 10, wherein the fired ceramic piece comprises magnesium oxide, titanium dioxide, and calcium oxide in a combined concentration of no more than about 0.3% by weight.

20. A method for manufacturing a ceramic biomedical implant, the method comprising the steps of:
preparing a slurry comprising ingredients configured to yield a ceramic piece comprising at least aluminum oxide, zirconium dioxide, yttrium oxide, cerium oxide, strontium oxide, magnesium oxide, titanium dioxide, and calcium oxide;
forming a compact derived from the slurry; and
firing the compact to obtain a fired ceramic piece comprising at least aluminum oxide, zirconium dioxide, yttrium oxide, cerium oxide, strontium oxide, magnesium oxide, titanium dioxide, and calcium oxide,
wherein the fired ceramic piece comprises aluminum oxide in a concentration of at least about 74.6% by weight,
wherein the fired ceramic piece comprises a combination of aluminum oxide, strontium oxide, magnesium oxide, titanium dioxide, and calcium oxide in a concentration of at least about 84% by volume,
wherein the fired ceramic piece comprises yttrium oxide in a concentration of between about 0.8% and about 1.5% by mole of the total molar amounts of zirconium dioxide, yttrium oxide, and cerium oxide in the fired ceramic piece,
wherein the fired ceramic piece comprises cerium oxide in a concentration of between about 1.75% and about 4.0% by mole of the total molar amounts of zirconium dioxide, yttrium oxide, and cerium oxide in the fired ceramic piece,
wherein the fired ceramic piece comprises strontium oxide in a concentration of between about 0.8% and about 1.2% by weight,
wherein the fired ceramic piece comprises strontium oxide in a concentration of about 0.8% by weight, and
wherein the fired ceramic piece comprises magnesium oxide, titanium dioxide, and calcium oxide in a combined concentration of no more than about 0.3% by weight.

21. A method for manufacturing a ceramic biomedical implant, the method comprising the steps of:
preparing a first feedstock by mixing ingredients comprising at least aluminum oxide and strontium carbonate or ingredients selected to yield aluminum oxide and strontium carbonate;
preparing a second feedstock by mixing ingredients comprising at least aluminum oxide and calcium carbonate or ingredients selected to yield aluminum oxide and calcium carbonate;
preparing a slurry comprising materials from the first feedstock, materials from the second feedstock, and further comprising additional ingredients configured to yield at least a portion of a ceramic biomedical implant comprising at least aluminum oxide, zirconium dioxide, yttrium oxide, cerium oxide, strontium oxide, magnesium oxide, titanium dioxide, and calcium oxide;
forming a compact derived from the slurry;
firing the compact to obtain a fired piece;
after the step of firing the slurry, compressing the fired piece; and
reoxidizing the fired piece, wherein, following the step of reoxidizing the fired piece, the fired piece comprises at least aluminum oxide, zirconium dioxide, yttrium oxide, cerium oxide, strontium oxide, magnesium oxide, titanium dioxide, and calcium oxide, and wherein the fired piece comprises strontium oxide in a concentration of between about 0.8% and about 1.2% by weight.

22. A method for manufacturing a ceramic piece, the method comprising the steps of:
preparing a slurry comprising ingredients configured to yield a ceramic piece comprising at least aluminum oxide, zirconium dioxide, yttrium oxide, cerium oxide, strontium oxide, magnesium oxide, titanium dioxide, and calcium oxide;
forming a compact derived from the slurry; and
firing the compact to obtain a fired ceramic piece comprising at least aluminum oxide, zirconium dioxide, yttrium oxide, cerium oxide, strontium oxide, magnesium oxide, titanium dioxide, and calcium oxide, wherein the fired ceramic piece comprises a combination of aluminum oxide, strontium oxide, magnesium oxide, titanium dioxide, and calcium oxide in a concentration of at least about 84% by volume.

* * * * *